United States Patent [19]

Kitagawa et al.

[11] Patent Number: 4,947,846
[45] Date of Patent: Aug. 14, 1990

[54] WATERPROOF ELECTRODE DEVICE FOR A LIVING BODY

[75] Inventors: Toshiyuki Kitagawa, Chiba; Namio Katoh, Ichikawa, both of Japan

[73] Assignee: TDK Corporation, Tokyo, Japan

[21] Appl. No.: 353,622

[22] PCT Filed: Jun. 10, 1988

[86] PCT No.: PCT/JP88/00560
§ 371 Date: Feb. 6, 1989
§ 102(e) Date: Feb. 6, 1989

[87] PCT Pub. No.: WO88/09643
PCT Pub. Date: Dec. 15, 1988

[30] Foreign Application Priority Data

Jun. 13, 1987 [JP] Japan .............. 62-91071[U]
Jun. 13, 1987 [JP] Japan .............. 62-91072[U]

[51] Int. Cl.⁵ .............................. A61B 4/408
[52] U.S. Cl. .................................... 128/640
[58] Field of Search ................. 128/639-641, 128/802, 803

[56] References Cited

U.S. PATENT DOCUMENTS

| 4,029,086 | 6/1977 | Corasanti | 128/641 |
| 4,112,941 | 9/1978 | Larimore | 128/641 |
| 4,259,965 | 4/1981 | Fukuda et al. | 128/640 |
| 4,270,543 | 6/1981 | Tabuchi et al. | 128/640 |
| 4,653,503 | 3/1987 | Heath | 128/640 |

FOREIGN PATENT DOCUMENTS

| 0007227 | 1/1983 | Japan | 128/640 |
| 131729 | 6/1986 | Japan . | |
| 59002 | 4/1987 | Japan . | |

Primary Examiner—Lee S. Cohen
Attorney, Agent, or Firm—Armstrong, Nikaido, Marmelstein, Kubovcik & Murray

[57] ABSTRACT

The present invention is characterized by a construction wherein a magnet is provided either to the connector or the ECG electrode, and a magnetic material or a magnet to the other, and both are stuck by magnetic attraction. Subsequently, a water penetration prevention sealing material, comprising a closed-cell type foam material, is interposed between the electrode case and the connector. Due to this construction, electric signals do not leak into the water and the connector is not pressed against the electrode.

8 Claims, 6 Drawing Sheets 4,947,846

WATERPROOF ELECTRODE DEVICE FOR A LIVING BODY

FIELD OF THE INVENTION

The present invention relates to an electrode device for a living body to be used for electrocardiographs, electroencephalographs, etc., and in particular, to be constructed so that electrical signals can be detected easily and correctly even in a warm bath, a cold bath, etc.

PRIOR ART

In recording and analyzing bioelectrical phenomena detected by the Electro-Cardio-Graph (ECG) and utilizing the data in diagnosis, it is essential to make a general judgement according to the bioelectric phenomena under various environmental conditions and to treat a patient more effectively. ECG signals obtained while the patient is taking a cold or warm bath, as one of the environmental conditions, are considered as important analysis material.

Conventional ECG electrode apparatus is shown, for example, in U.S. Pat. No. 4,029,086. A hook type as shown in FIG. 1 or an alligator clip type has been extensively used.

The hook type ECG electrode apparatus will be described with reference to FIG. 1. Adhesive 20 is applied on an adhesion sheet 21 comprising a disk-shaped foam material to stick the sheet 21 to a human body conductive mandrel 23 integral with an electrode 22 is passed through the center hole 24 of the sheet 21. A sponge 25 impregnated with conductive gel is stuck to the electrode 22. A male terminal 26 of the metallic hook is fixed on the mandrel 23. On the other hand, a female terminal 27 comprising an elastic material is formed integral with a synthetic resin connector main body 28. A soldered part 30 of the end part of a lead wire 29 and the female terminal 27 are formed integral with the connector main body 28.

Since the terminals 26, 27 are exposed, a conventional ECG electrode apparatus of the hook or alligator clip type has the disadvantage of electrical signal leakage in water , hence it is not suitable for the detection of electric signals. In addition, since the connector main body 28 must be pressed when connecting the connector and the electrode, the conducting gel in the sponge 25 is squeezed out.

The object of the present invention is to overcome such disadvantages of conventional ECG electrodes.

SUMMARY OF THE INVENTION

The present invention is characterized by a construction wherein a magnet is provided either to the connector or the ECG electrode, and a magnetic material or a magnet to the other, and both are stuck by magnetic attraction. Subsequently, construction wherein a water penetration prevention sealing material comprising closed-cell type foam material is interposed between the electrode case and the connector. Due to this construction, electrical signals do not leak into the water and the connector is not pressed against the electrode.

DESCRIPTION OF THE PREFERRED EMBODIMENT

Figure 1:
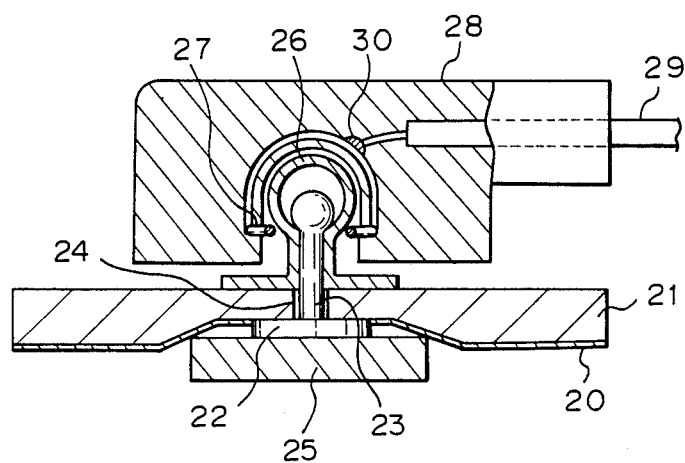
FIG. 1 is a sectional view of conventional ECG electrode apparatus.
Figure 2:
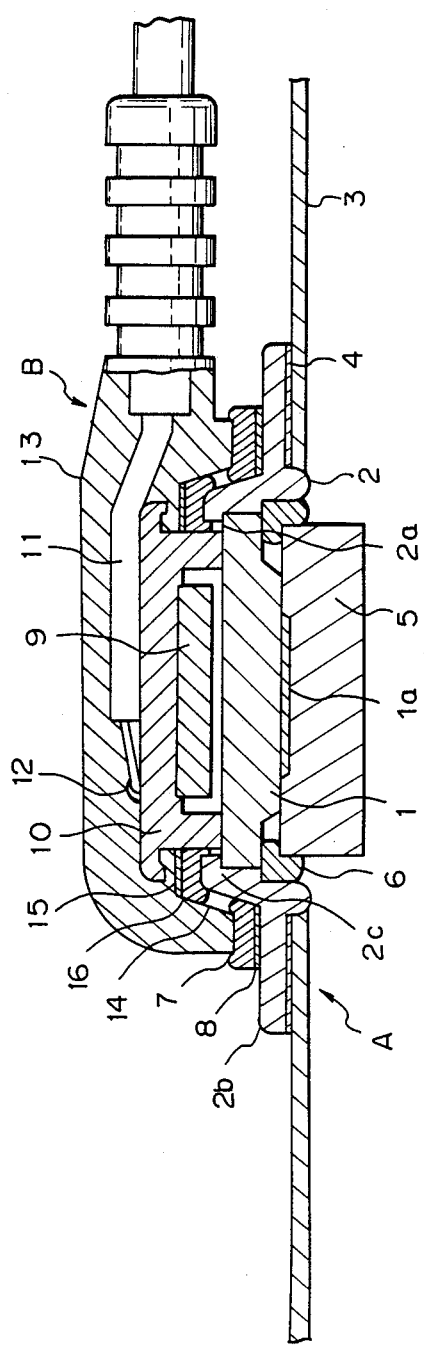
FIG. 2 is a vertical sectional view showing the connector and the electrode in the connected state in an embodiment of the ECG electrode apparatus according to the present invention.
Figure 3A:
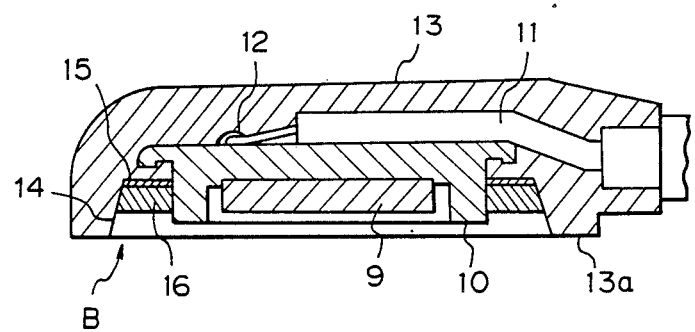
FIG. 3 is a sectional view showing the state before use.
Figure 3B:
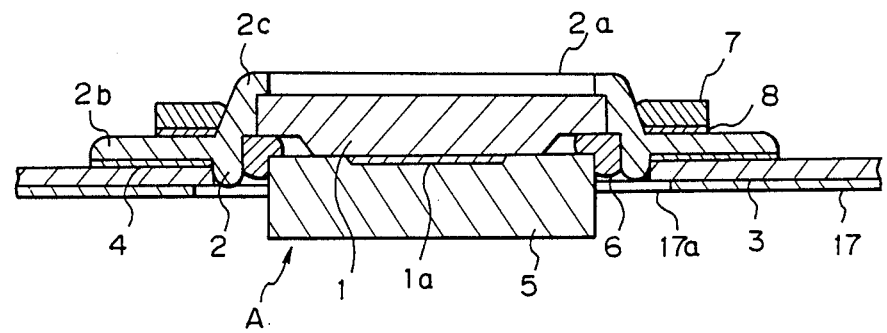

An embodiment of the present invention will be described with reference to FIGS. 2 to 5. FIG. 2 is a vertical sectional view showing the ECG electrode apparatus according to the present invention. FIG. 3 is a sectional view of the apparatus in the condition before use. In FIGS. 2 and 3, A is an ECG electrode, and B is a connector. The ECG electrode A is a conductor in which an electrode 1a made of, for example, silver chloride is fixed and holds a circular electrode base 1 made of magnetic material at the central opening part 2a of a circular electric insulation case 2 made of synthetic resin. An adhesive sheet 3 for sticking to a human body is fixed to the case 2 using adhesive 4 or the like. A sponge impregnated with conductive gel is laid on the electrode base 1. The sponge 5 is fixed to the case 2 by the adhesive 6 together with the electrode 1a and the electrode base 1. 7 is a water penetration preventing sealing material made of a ring-shaped foam-material according to the present invention and is fixed to the top surface of an edge part 2b of the case 2 with adhesive 8. For the foam material used as the sealing material 7, foam plastic such as polystyrene, polyurethane, vinyl chloride resin, polyethylene, etc, or sponge rubber or the like is used. To enhance the sealing property, closed-cell type material is used. As shown in FIG. 5, water penetration prevention is promoted by applying water repellent 7a on the surface of the sealing material 7, preferably on both sides as shown.

On the other hand, the connector B has a permanent magnet 9 (for example of ferrite material) attracting the electrode base 1 made of the aforementioned magnetic material. The permanent magnet 9 is held in an electroconductive circular yoke 10. A lead wire 11 for connecting an external measuring instrument is soldered (12) to the circular yoke 10. The connector B is formed so that a part of the yoke 10 and the soldered part 12 integrally formed and covered by a connector main body 13 made of synthetic resin and having electrical insulation properties. The outer dimension of the yoke 10 is such that the portion exposed from the connector main body 13 is slightly smaller than the inner dimension of an opening part 2a provided in the case 2.

In the bottom circumference of the connector main body 13, a round projection 13a is formed (FIG. 3), a circular recess 14 is formed between the projection 13a and the yoke 10, and a ring-form sealing material 16 made of the same closed-cell type foam material as the sealing material 7 is fixed to the round hollow part 14 with adhesive 15. The round hollow part 14 and the seal material 16 are provided in the portion corresponding to a round projection 2c around the central opening part 2a of the case 2 of the ECG electrode A.

The ECG electrode A is disposable, and the adhesion sheet 3 protects its adhesive application surface by sticking to a parting paper 17 (refer to FIG. 3), the sponge 5 is inserted to the opening part 17a provided in the parting paper 17, an airtight tray-like sheet to be adhered to the rear side of the parting paper 17 is laid on the sponge 5, and the entire ECG electrode A is peeled from the parting paper 17 before use.

According to this arrangement, as shown in FIG. 2, when the yoke 10 is inserted to the opening part 2a of the case 2 and abutted to the electrode base 1 made of magnetic material, the electrode base 1 is attracted by the permanent magnet 9, and the connector B is connected to the ECG electrode A. In this case, the connector B is not to be pressed against the ECG electrode A. At this time, the projection 13a of the connector main body is pressed against the seal material 7 by the magnetic attraction, and at the same time the projection 2c of the case 2 is pressed against the sealing material 14. Accordingly, the entry of water between the two is prevented.

Figure 4:
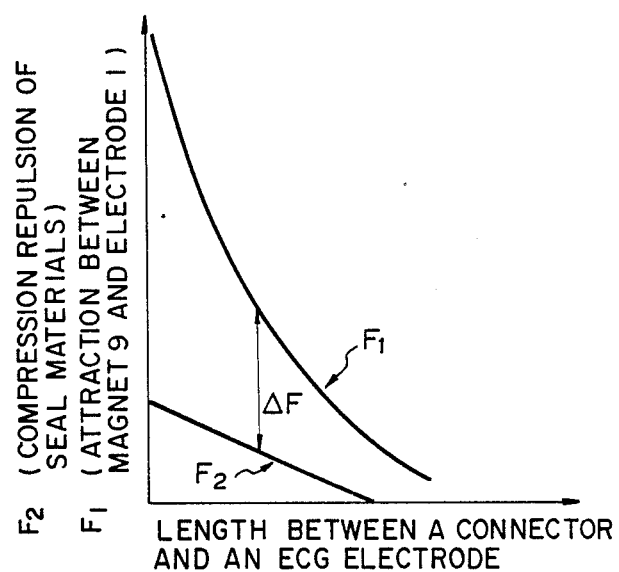
FIG. 4 is a view showing the relationship of the attraction of the magnet and the electrode base to the distance between the connector and the ECG electrode and the relationship of the compression repulsion of the seal material to the distance between the connector and the ECG electrode.
Figure 5:
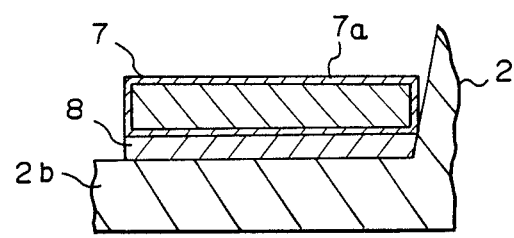
FIG. 5 is an enlarged sectional view showing an example of the sealing material.

FIG. 4 is a graph showing the relationship between the attraction $F_1$ the magnet 9 and the electrode base 1 to the distance between the connector B and the ECG electrode A and the relationship between the compression repulsion $F_2$ of the seal materials 7, 16 to the distance between the connector B and the ECG electrode A. As will be understood from the graph, while the magnetic attraction $F_1$ is inversely proportional to the distance between the connector B and the ECG electrode A, the compression repulsion $F_2$ of the seal member 7, 16 linearly decreases, and the decrease in the difference of the attraction $\Delta F$ between $F_1$ and $F_2$ is small in spite of the increase of the distance between the connector B and the ECG electrode A. Due to this, a wide allowable range for the variation in the repulsion of the seal member 7, 16 or a wide allowable range for the dimensions of the seal member 7, 16 can be taken and a stable sealing property can be obtained.

On the other hand, by using a closed-cell type foam material as the seal member 7, 16, the insulation resistance drop through the layer comprising the seal member 7, 16 by water penetration can be prevented.

Furthermore, when the seal member 7 or 16 is fixed in advance to the case 2 or the connector main body 13 as in this embodiment, when the connector B is connected to the ECG electrode A utilizing the magnetic attraction, the two can be connected easily by a one-touch operation, water-proofing properties can be obtained, and operability is good.

Furthermore, according to the present embodiment, since the arrangement is such that the seal member 16 is provided at the circular recessed part 14 provided in the connector B and the seal member 16 is compressed by the projection 2c of the case 2 of the ECG electrode A fitted to the circular recessed part 14, the seal member 16 and the projection 2c are correctly in position, and a complete sealing effect can be obtained. In addition, when the two seal members 7 and 16 are provided as in the present embodiment, even if water penetrates into the large diameter ring-like seal member 7 on the outer circumference side, further water penetration to the inside can be prevented by the small diameter ring-like seal member 16 provided on the inner circumference side. Subsequently, a more complete sealing effect can be obtained as compared with the case where only either one of the two is provided.

In the above embodiment, although an arrangement is made for the magnet 9 to attract the electrode base 1 comprising the magnetic member 1, a magnet may be used in lieu of the magnetic member 1. It is to be expressly understood that many other modifications and additions regarding the shape and structure of each component part may be made without departing from the spirit and the scope of the present invention.

Now, a different embodiment of the electrode A according to the present invention will be described with reference to FIGS. 6 through 8.

In the embodiment shown in FIG. 2, using non-woven fabric as an adhesive sheet 3 provides a better adaptation to the human body and is preferable in that it improves gas permeability and water permeability, however, when this ECG electrode is used for diagnosis while a patient is taking a bath or the like, even if the portion between the electrode and the connector (not shown) is water-proofed, water will penetrate to the portion of the sponge 5 or the electrode base 1 by capillary action at the adhesive sheet 3 (non-woven fabric), and there is a possibility of electrical signal leakage.

On the other hand, as a material to prevent water penetration, closed-cell type foam material can be used in lieu of the adhesive sheet 3. While this foam material is excellent in terms of water-proof properties, it lacks gas permeability and water permeability. Thus sweat generated while taking a bath collects between the skin and the foam material. This sweat may form an electrical path between the conductive gel impregnated in the sponge 5 and the external cold water or warm water. The collection of this sweat and conductivity are further aggravated by the area of the foam material increased to strengthen the adhesiveness (the foam material is weak in adhesion properties and poor adaptability to the skin due to its large thickness.

Figure 6:
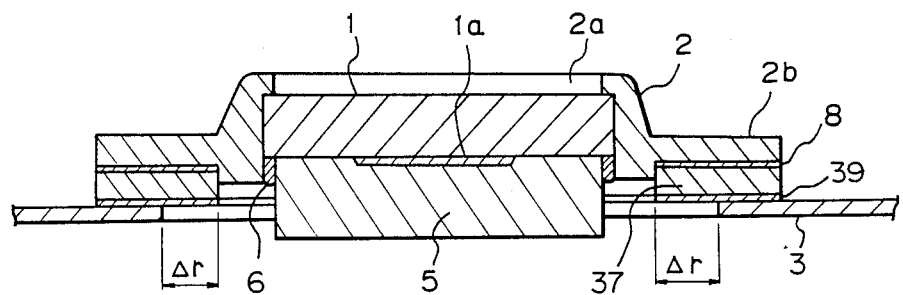
FIG. 6 is a sectional view of the ECG electrode according to the present invention.
Figure 7:
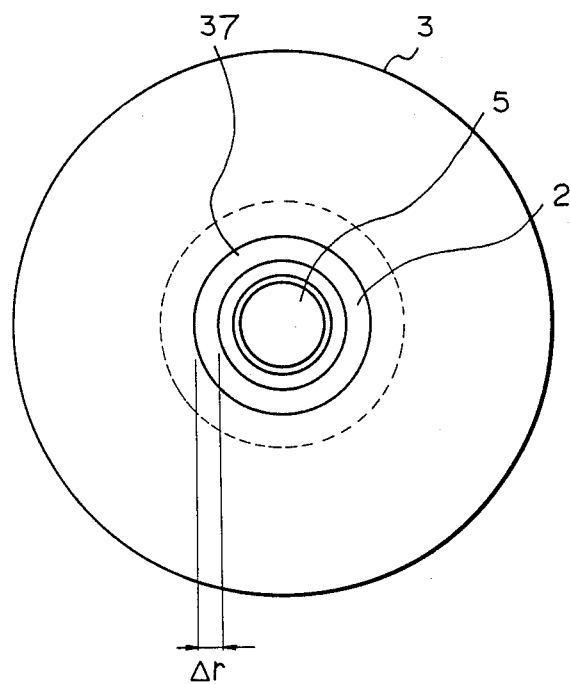
FIG. 7 is a bottom view of FIG. 6.

FIG. 6 is a sectional view of an ECG electrode that can solve the above problem. FIG. 7 is a bottom view of the above. In FIGS. 6 and 7, an ECG electrode holds a circular electrode base 1 made of magnetic material of ferrite or the like to be attracted by a magnet provided with a connector (not shown) at the opening part 2a of a circular case 2. An electrode 1a of silver chloride or the like is fixed to the elctrode base 1. An adhesive sheet 3 of a circular shape or other shapes to stick to the human body is fixed to the case 2 using adhesive 4 or the like. A sponge 5 impregnated with conductive gel is superimposed on the electrode base 1, and the sponge 5 is fixed to the case 2 by adhesive 6 together with the electrode 1a and the electrode base 1. 37 is a ring-shaped sheet of non-water-permeable properties fixed to the under side of a circumferential part 2b of the electrode case 2 using adhesive 8 or the like. The sheet is made of closed-cell type foam material. Adhesive 39 to stick to the human body is applied to the underside of the sheet 37. As a foam material composing the sheet 37, foam plastics, such as polystyrene, polyurethane, vinyl chloride resin, polyethylene or the like, or sponge rubber or the like are used.

The adhesive sheet 3 is made of a material such as non-woven fabric or the like which is excellent in terms of gas permeability and water permeability and is stuck to the underside of the outer circumferential side except for the portion of the inner circumferential side $\Delta r$ of the underside of the sheet 37 with the adhesive 39 or the adhesive applied to the adhesive sheet 3.

Acoording to this arrangement, when a warm or cold bath test is performed with the adhesive sheet 3 and the sheet 37 stuck to the human body, even if water (including warm water) penetrates from the outside to the inside by capillary action along the adhesive sheet 3, water permeation is prevented by the non-permeable sheet 37, water penetration to the portion of sponge 5 is prevented, and the electrical connection between the conductive gel in the sponge and the outside water is prevented.

Even if sweat is generated between the adhesive sheet 3 and the human body or between the sheet 37 and the human body, the sweat is absorbed by the water-permeable adhesive sheet 3, and released outside without being collected.

Figure 8:
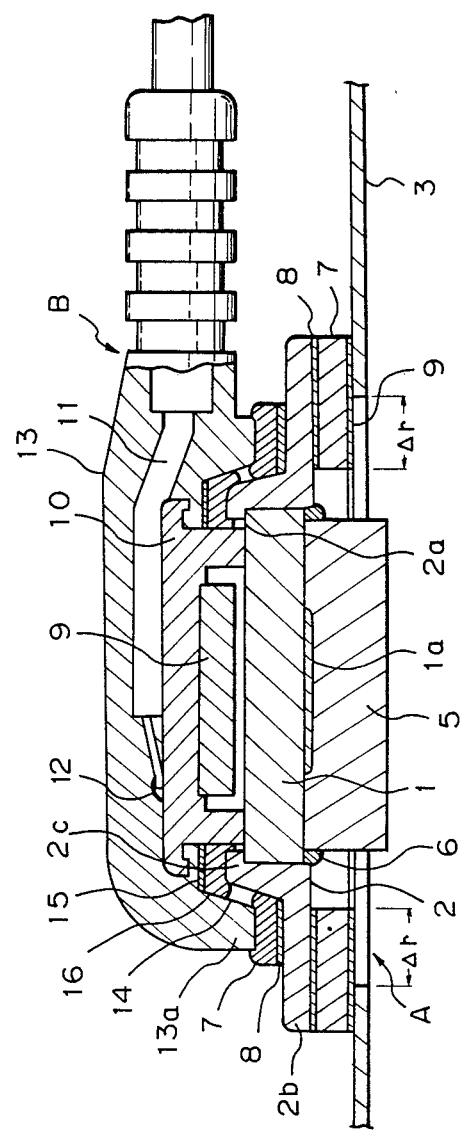
FIG. 8 is a sectional view of the ECG electrode apparatus using the ECG electrode of FIG. 6.

FIG. 8 is a sectional view of a water-proof ECG electrode apparatus using an ECG electrode of FIG. 6. The ECG electrode A fixes a ring-shaped seal member 7 of closed-cell type to the top surface of a circumferential part 2b of the electrode with adhesive 8. A connector B uses a permanent magnet 9 which attracts an electrode base 1 made of the magnetic material, and holds the permanent magnet 9 by a circular yoke 10. An external instrument connection lead wire 11 is soldered (12) to the circular yoke 10. The connector B is constructed by a portion of the yoke 10 and the soldered part 12 being integrally formed and covered by a connecter main body 13 of electrical insulation properties made of synthetic resin. The outside diameter of the yoke 10 is such that the portion exposed from the connector main body 13 is made slightly smaller than the inside diameter of the opening part 2a provided in the case 2, and it is so arranged that the yoke 10 and the electrode base 1 are attracted mutually in contact as shown.

A circular projecting part 13a is formed around the underside of the connector main body 13, a circular recessed part 14 is formed between the projecting part 13a and the yoke 10, and a ring-shaped seal member 16 made of closed-cell type foam material is fixed to the circular recessed part 14 with adhesive 15. The circular recessed part 14 and the seal memeber 16 are provided at portions corresponding to a circular projecting part 2c around the central opening part 2a of the case 2 of the ECG electrode A.

According to the arrangement, as shown, by inserting the yoke 10 to the opening part 2a of the case 2 and abutting it to the electrode base 1 made of magnetic material the electrode base 1 is attracted by the permanent magnet 9, and the connector B is connected to the ECG electrode A. In this case, the connector B does not need to be pushed against the ECG electrode A. At the same time, the projecting part 13a of the connector main body 13 is pressed to contact with the seal member 7 by the magnetic attraction, and the projecting part 2c of the case 2 is pressed to contact with the seal member 16. Accordingly, water entry between the two is prevented.

By fixing the seal member 7 or 14 to the case 2 or the connector main body 13 in advance, when connecting the connector B to the ECG electrode A by utilizing magnetic attraction, connection can be accomplished by just a one-touch operation, water-proof properties can be obtained, and operability can be improved.

In addition, since the arrangement is such that, as shown, the seal member 16 is provided in the circular recessed part 14 provided in the connector B and seal member 16 is compressed by the projecting part 2c of the case 2 of the ECG electrode A which is to be fitted into the circular recessed part 14, there is no positional displacement between the seal member 16 and the projecting part 2c, and an assured sealing effect can be obtained. In addition, if two seal members 7 and 16 are provided, even if water penetration has occurred through the outer circumference side large diameter ring-shaped seal member 7, further water penetration to the inside is prevented by the inner circumference side small diameter ring-shaped seal member 16, and a more positive sealing effect can be obtained compared with the case where either one of the seal members is provided. Alternatively, by applying water repellent on the surface of the seal member 16 or 7 to improve its sealing properties, water penetration is further resisted. The sealing by either one is possible, and the structure is simplified accordingly.

Though in the above embodiment the adhesive sheet 3 is fixed to the underside of the sheet 37, the adhesive sheet 3 may be fixed by holding the inner circumferential part of the adhesive sheet 3 between the sheet 37 and the circumferential part 2b. In addition, in performing the present invention, many modifications and alternatives of the shape and structure of components can be made without departing from the spirit and the scope of the present invention.

APPLICATION TO INDUSTRY

As heretofore described, according to the present invention, a magnet is provided to either one of the connector and the ECG electrode and a magnetic material or a magnet is provided to the other to bring the two into contact by the action of magnetic attraction, and a water-proof seal member made of a closed-cell type foam material is interposed between the electrode case and the connector. By this arrangement, water penetration between the ECG electrode and the connector can be prevented, and a water-proof ECG electrode apparatus with which a person (patient) in cold or warm water can be diagnosed can be provided.

In addition, according to the present invention, from the relationship between the magnetic attraction and repulsion due to the elasticity of the seal member, almost the same attraction is obtained regardless of the change in the distance between the two, therby giving a stable electrically connected relationship regardless of the variation of dimensions, etc. of the seal member.

In addition, since a seal member of closed-cell type is used, water penetration through the seal member can be prevented.

In addition, since magnetic attraction is utilized to bring the ECG electrode and the connnector into contact, no stress need be applied for the connector connection, thereby eliminating flow-out of conductive gel at the time of connector connection.

In addition, a ring-shaped non-water-permeable water-proof sheet is fixed to the underside of the circumferential part of the electrode case holding the electrode and a sponge impregnated with conductive gel and the inner circumferential part of the water-permeable adhesive sheet is fixed to the outer circumferential side of the sheet, water penetration into the adhesive sheet of the ECG electrode can be prevented, the conductive gel in the sponge and external water are prevented from communicating electrically, and a water-proof ECG electrode capable of testing a person (patient) in cold or warm bath can be provided.

In addition, even if sweat is generated between the adhesive sheet and the human body or between the water-proof sheet and the human body, the sweat is absorbed in the water-permeable adhesive sheet and does not collect.

In addition, since the adhesive sheet is flexible, it tends to adapt itself to the human body, no separation occurs, and its size can be miniaturized.

Thus, the apparatus according to the present invention can be used extensively as an ECG electrode to be used for electrocardiographs and electroencephalographs that can be used while a patient is taking a bath.

What is claimed is:

1. A water-proof electrode device comprising:
   an ECG electrode including
     an electrode,
     an electrode base of a magnetic material, said electrode fixed on said electrode base, and
     an electrode case accommodating said electrode and electrode base with said electrode exposed for detecting signals from a living body;
   a connector for electrically connecting said electrode to a recording device including
     a permanent magnet magnetically attracted to said electrode base, and
     a connector main body accommodating said permanent magnetic; and
   water penetration prevention seal members made of a closed-cell type foam material interposed between said electrode case and said connector main body to preclude entry of water between the case and main body.

2. A water-proof electrode device according to claim 1 wherein the seal members are fixed to the electrode case.

3. A water-proof electrode device according to claim 1 wherein the seal members are fixed to the connector main body.

4. A water-proof electrode device according to claim 1 wherein the electrode case has a circular projecting part projecting to a side of the connector main body, said circular projecting part surrounds a center opening part of said electrode case, the connector main body has a circular recessed part in which the circular projecting part fits, the seal members comprises a large diameter and a small diameter ring-shaped seal member, the large diameter ring seal member is fixed to an edge part of the electrode case, and the small diameter seal member is fixed to the circular recessed part.

5. A water-proof electrode device according any one of claims 1, 2, 3, or 4 wherein a water-repellent material is applied on one or both of the seal members.

6. A water-proof electrode device according to claim 1 wherein the electrode has a non-water-permeable ring-shaped water-proof sheet fixed to an underside of a circumferential part of the electrode case, said electrode case having the electrode and having a sponge impregnated with conductive gel on the electrode, and an outer circumferential side of the waterproof sheet having fixed thereto an inner circumferential part of a gas-and-water-permeable adhesive sheet.

7. A water-proof ECG electrode device according to claim 6 wherein the gas-and-water-permeable adhesive sheet is non-woven fabric.

8. A water-proof electrode device according to claim 1 wherein the electrode case has a circular central opening part and the connector includes a circular yoke provided thereunder inserted into the central opening part.

* * * * *